US009228986B2

(12) United States Patent
Xiao et al.

(10) Patent No.: US 9,228,986 B2
(45) Date of Patent: Jan. 5, 2016

(54) SIMULTANEOUS DETERMINATION OF MULTIPLE ANALYTES IN INDUSTRIAL WATER SYSTEM

(75) Inventors: Caibin Xiao, Holliston, MA (US); Bingzhi Chen, Bensalem, PA (US); Chunbo Yu, Shanghai (CN); Hong Xu, Shanghai (CN)

(73) Assignee: General Electric Company, Schenectady, NY (US)

( * ) Notice: Subject to any disclaimer, the term of this patent is extended or adjusted under 35 U.S.C. 154(b) by 130 days.

(21) Appl. No.: 13/059,139

(22) PCT Filed: Aug. 3, 2010

(86) PCT No.: PCT/CN2010/001170
§ 371 (c)(1),
(2), (4) Date: Feb. 15, 2011

(87) PCT Pub. No.: WO2012/016350
PCT Pub. Date: Feb. 9, 2012

(65) Prior Publication Data
US 2013/0122597 A1   May 16, 2013

(51) Int. Cl.
*G01N 21/78* (2006.01)
*G01N 21/80* (2006.01)
(Continued)

(52) U.S. Cl.
CPC ............... *G01N 31/22* (2013.01); *G01N 21/78* (2013.01); *G01N 21/80* (2013.01); *G01N 31/221* (2013.01); *G01N 33/18* (2013.01); *G01N 33/182* (2013.01); *Y10T 436/16* (2015.01); *Y10T 436/193333* (2015.01)

(58) Field of Classification Search
None
See application file for complete search history.

(56) References Cited

U.S. PATENT DOCUMENTS 3,701,633 A * 10/1972 Davis ........................... 422/408
4,409,182 A    10/1983 Macklem
(Continued)

FOREIGN PATENT DOCUMENTS

CN       1940553 A    4/2007
CN     101675331 A    3/2010
(Continued)

OTHER PUBLICATIONS

International Search Report and Written Opinion mailed May 19, 2011 for PCT/CN2010/001170 filed Aug. 3, 2010.
(Continued)

*Primary Examiner* — Yelena G Gakh
*Assistant Examiner* — Michelle Adams
(74) *Attorney, Agent, or Firm* — Wegman, Hessler & Vanderburg

(57) ABSTRACT

A method using a multi-purpose reagent composition to simultaneously determine concentrations of at least two analytes in a water sample. In one embodiment, the multi-purpose reagent composition used is for simultaneously determining free chlorine concentration and pH and comprises a free chlorine sensitive dye and a pH indicator. In another embodiment, the reagent composition used is for simultaneously determining of free chlorine and anionic polymer and includes a free chlorine sensitive dye, a pH buffer, a cationic dye, and an organic co-solvent. Thus, the pairs of free chlorine and pH or free chlorine and anionic polymer are determined using a single reagent composition. The reagent composition can also be the main reagent for one analyte analysis when it is used alone and also function as an ancillary reagent when it is combined with a second reagent composition for the determination of another analyte.

16 Claims, 15 Drawing Sheets

SPECTRAL RESPONSE OF THE ALL-IN ONE REAGENT TO CHLORINE/HPSI MIXTURES.

(51) Int. Cl.
*G01N 31/22* (2006.01)
*G01N 33/18* (2006.01)

(56) References Cited

U.S. PATENT DOCUMENTS

| | | | |
|---|---|---|---|
| 4,904,605 A * | 2/1990 | O'Brien et al. | 436/169 |
| 5,958,778 A | 9/1999 | Kidd | |
| 5,972,713 A | 10/1999 | Kuzuhara et al. | |
| 6,121,050 A * | 9/2000 | Han | 436/95 |
| 6,214,627 B1 | 4/2001 | Ciota et al. | |
| 6,413,473 B1 * | 7/2002 | Bacon | 422/408 |
| 2004/0219620 A1 | 11/2004 | Mayer | |
| 2007/0072305 A1 | 3/2007 | Mitsumoto | |
| 2008/0299665 A1 * | 12/2008 | Xiao et al. | 436/85 |
| 2009/0098022 A1 | 4/2009 | Tokhtuev et al. | |

FOREIGN PATENT DOCUMENTS

| | | |
|---|---|---|
| CN | 101765772 A | 6/2010 |
| WO | WO 92/12424 A1 | 7/1992 |
| WO | WO 2007/050463 A1 | 5/2007 |

OTHER PUBLICATIONS

International Preliminary Report on Patentability mailed Feb. 5, 2013 for PCT/CN2010/001170 filed Aug. 3, 2010.
European Search Report and European Search Opinion mailed Mar. 27, 2014 for EP 10 85 5488.

* cited by examiner

FREE CHLORINE DECAY IN THE PRESENCE OF AMMONIUM CHLORIDE.

SPECTRAL RESPONSE OF THE ALL-IN ONE REAGENT TO HPSI.

ABSORBANCE AT 467 nm AS A FUNCTION OF CHLORINE CONCENTRATION.

SPECTRAL RESPONSE OF THE ALL-IN ONE REAGENT TO FREE CHLORINE AT pH AROUND 7.6

SPECTRAL RESPONSE OF THE COMPOSITE REAGENT TO FREE CHLORINE AT pH AROUND 8.0

SPECTRAL RESPONSE OF THE COMPOSITE REAGENT TO FREE CHLORINE AT pH AROUND 9.0

SIMULTANEOUS DETERMINATION OF MULTIPLE ANALYTES IN INDUSTRIAL WATER SYSTEM

BACKGROUND OF THE INVENTION

1. Field of the Invention

This invention relates generally to a method and reagent composition for simultaneous determination of at least two analytes in water samples with a single stable reagent composition containing at least two colorimetric reagents and auxiliary reagents such as buffer and masking reagent. The reagent composition can be formulated to have multiple functions including (1) clearing the deposition in the fluidic system, (2) pH buffering, and (3) acting as an auxiliary reagent to assist other analyte analysis that uses other reagents delivered within the same fluidic system.

2. Description of Related Art

Water is used in a number of industrial water systems such as cooling and boiler water systems. Municipal or untreated water contains impurities that can affect heat transfer, fluid flow, or cause corrosion of system equipment. For example, metal cations such as calcium, magnesium, barium and sodium are often present in untreated water. When the water contains an excess of these impurities, precipitates can form on equipment surfaces in the form of scales or deposits. The presence of these scales or deposits adversely affects the rate of heat transfer, and therefore the efficiency of the system. Furthermore, the cleaning or removal of such scales or deposits is expensive and burdensome because it typically requires a shutdown of the system. Accordingly, before the water is utilized for cooling or steam purposes, it is desirably treated with appropriate chemicals in order to inhibit scale formation.

It is known, for example, to add anionic water-soluble polymers to the water. One particularly useful water-soluble polymer is HPS-I (polymer of acrylic acid/1-allyoxy, 2-hydroxypropylsulfonate), although other water-soluble polymers such as AEC (polyepoxysuccinic acid) and APES (ammonium allylpolyethoxy sulfate) are in use as well. However, the employment of water-soluble polymers in industrial water systems presents its own set of problems because the concentration of the polymers in the water must be carefully monitored. For example, if too little of the polymer is employed, scaling and deposition will occur. In contrast, if too high a concentration of the polymer is employed, the cost/performance efficiency of the system is adversely affected. Additionally, chlorine is used to prevent biofilm formation in the tower. As with other methods of chemically treating aqueous systems, there is an optimal concentration of treatment chemicals that should be maintained. Monitoring and control of the industrial water chemistry is essential for maintaining proper performance and prolonging the life of the cooling tower and associated equipment.

Thus, it is understood that it is necessary to measure concentrations of multiple chemical and biological species in the industrial water, such as free chlorine, total chlorine, HPSI, and phosphate. Additionally, the pH of the water is controlled. Typically, operators rely on colorimetric analyzers based on known wet chemical analysis methods to monitor and control the water chemistry. For example, there are several colorimetric methods for determination of polyelectrolytes using dyes. One example is U.S. Pat. No. 6,214,627 issued to Ciota et al. In addition, there is a Hach polyacrylic acid method that uses iron thiocyanate chelation to detect calibration based on polyacrylic acid. Generally, these methods require a complicated, multi-step operation procedure and are difficult to carry out in the field. Other methods, such as the one disclosed in U.S. Pat. No. 5,958,778 issued to Johnson et al., use luminol-tagged polymers in combination with fluorescent or chemiluminescent detection techniques to monitor the industrial waters.

U.S. Pat. No. 5,972,713 discloses a method for determining total chlorine in a water sample using N-sulfoalkyl 3,3', 5,5'-tetramethylbenzidine (TMB-NSA). The total chlorine concentration is visually determined by changes in the color and hue of the test solution. U.S. patent application Ser. No. 11/523,021 discloses a method for determining residual chlorine in a water sample by a kit using TMB-NSA in a composition containing 3.5% sulfuric acid and alcohol to prevent the TMB-NSA from being crystallized and separating from the solution. In other colorimetric analyzers, a reagent is used for the determination of a single analyte, such as in the vanadomolybdate-based method for phosphate detection. It is seen that in most commercially available analyzers, at least one separate reagent is usually required for the determination of each analyte being measured. Previously, analyzers that use only a single reagent to determine multiple-analyte concentrations in the industrial environment have not been available.

One advantage of using a single reagent to determine multiple analyte concentrations is that the cost associated with analyzing two species is essentially the same as for a single species. Reducing the number of reagents typically required by the conventional online colorimetric analyzer also would improve instrument reliability because the number of reagent pumps and other fluidic components could be reduced. Moreover, the cost associated with reagent production, storage, transportation, and service may be reduced. Since the auxiliary reagents such as buffer are shared, liquid waste generated by an analyte using a combined reagent formulation of multiple analytes is also reduced.

Thus, there exists a strong need for simplified sensors and test methods that can easily be used to determine the concentration of multiple analytes, such as anionic polymer, phosphate, free chlorine, and total chlorine, and measure pH, using a single reagent in aqueous systems with high reproducibility, decreased response to interferences, and enhanced stability.

SUMMARY OF THE INVENTION

One aspect of the invention is directed to a multi-purpose reagent composition for simultaneously determining concentrations of at least two analytes in a water sample. The two analytes are selected from the group consisting of free chlorine, pH, anionic polymer, and phosphates. In one embodiment, the multi-purpose reagent composition is for simultaneously determining the concentration of free chlorine and pH and comprises a free chlorine sensitive dye and pH indicator. In another embodiment, the reagent composition is for simultaneously determining of free chlorine and anionic polymer and includes a free chlorine sensitive dye, a pH buffer, cationic dye, and organic co-solvent. Thus, the pairs of free chlorine and pH or free chlorine and anionic polymer are determined using a single reagent composition.

Another aspect of the invention is directed toward reagent sharing in which a reagent composition has at least two different functions. The reagent composition is the main reagent for one analyte analysis when it is used alone. The reagent composition also functions as an ancillary reagent when it is combined with a second reagent composition for the determination of another analyte. The method and reagent formulations are not only ideally suitable for online analyzer applications but also for offline, discrete, manual analysis of multiple analytes in water samples.

Another aspect of the invention is directed toward a method of simultaneously determining the concentrations of at least two analytes in a water sample using a multi-purpose reagent composition. The method includes adding a multi-purpose reagent composition to an aqueous sample and determining the concentration of at least two analytes in the aqueous sample, wherein the two analytes are selected from the group consisting of free chlorine, pH, anionic polymer, and phosphates. In one embodiment, the method simultaneously determines the concentration of free chlorine and pH using a single reagent composition that includes a free chlorine sensitive dye and pH indicator. In another embodiment, the method simultaneously determines free chlorine and anionic polymer using a single reagent that includes a free chlorine sensitive dye, a pH buffer, cationic dye, and organic co-solvent.

The present invention and its advantages over the prior art will become apparent upon reading the following detailed description and the appended claims with reference to the accompanying drawings.

BRIEF DESCRIPTION OF THE DRAWINGS

The above mentioned and other features of this invention will become more apparent and the invention itself will be better understood by reference to the following description of embodiments of the invention taken in conjunction with the accompanying drawings, wherein.

Corresponding reference characters indicate corresponding parts throughout the views of the drawings.

DETAILED DESCRIPTION OF THE INVENTION

Figure 1:
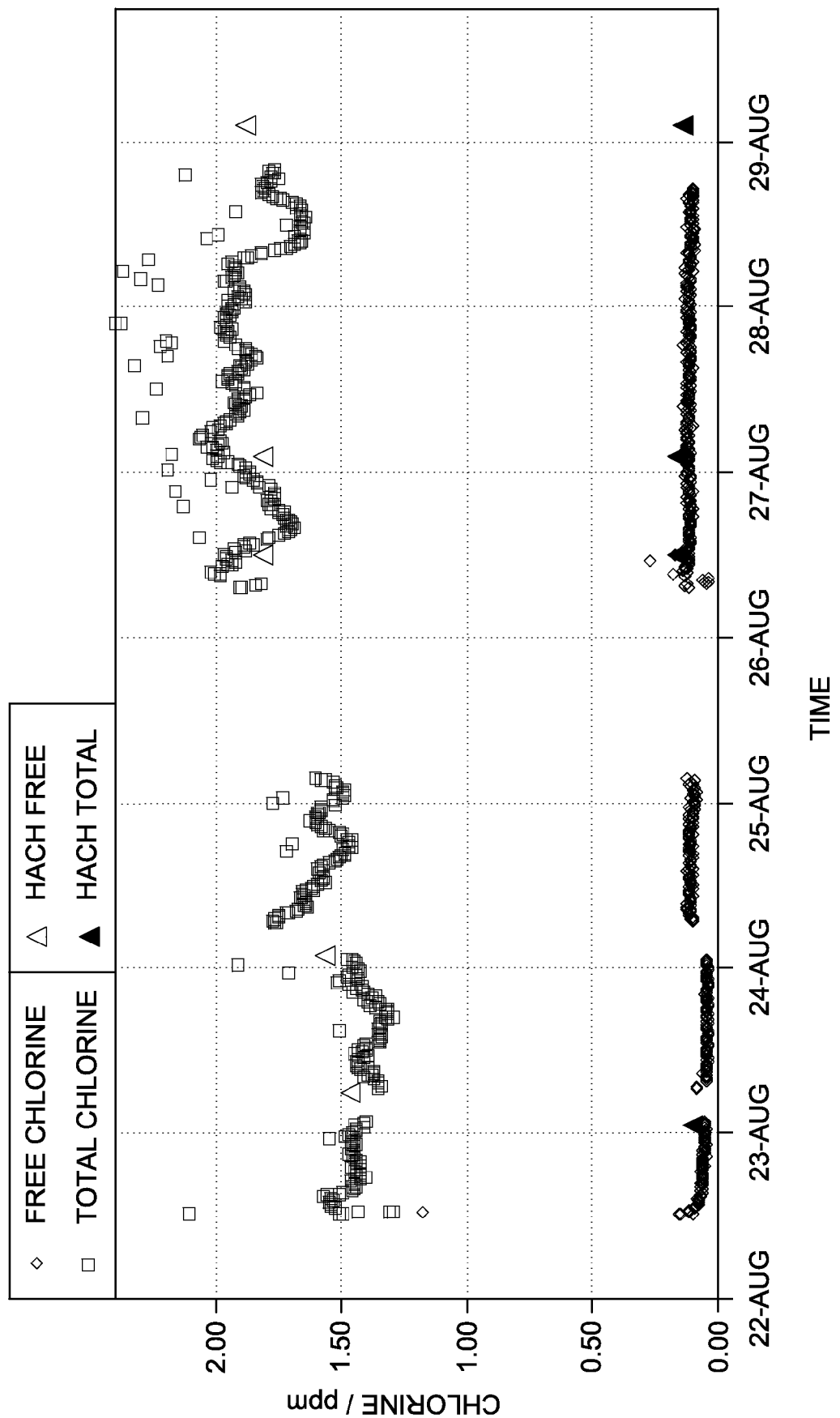
FIG. 1 is a graph showing free and total chlorine concentrations measured according to an embodiment of the invention.

The invention will now be described in the following detailed description with reference to the drawings, wherein preferred embodiments are described in detail to enable practice of the invention. Although the invention is described with reference to these specific preferred embodiments, it will be understood that the invention is not limited to these preferred embodiments. To the contrary, the invention includes numerous alternatives, modifications and equivalents as will become apparent from consideration of the following detailed description.

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges included herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

As used herein, the terms "comprises," "comprising," "includes," "including," "has," "having" or any other variation thereof, are intended to cover a non-exclusive inclusion. For example, a process, method, article or apparatus that comprises a list of elements is not necessarily limited to only those elements, but may include other elements not expressly listed or inherent to such process, method article or apparatus. The singular forms "a," "an" and "the" include plural referents unless the context clearly dictates otherwise.

Embodiments of the present invention are directed to improved methods for determining the concentration of multiple analytes in a water sample. According to one aspect of the invention, multiple analytes in a water sample can be determined using a single multi-purpose reagent composition. For example, in one embodiment, the pairs of free chlorine and pH or free chlorine and anionic polymer are determined using a single reagent composition. In another embodiment, the reagent composition performs at least two different functions. The reagent composition is the main reagent for one analyte analysis when it is used alone. The reagent composition also functions as an ancillary reagent when it is combined with a second reagent composition for the determination of another analyte. Accordingly, varying the reagents and sample mixing sequence enables multiple analytes to be measured simultaneously or sequentially. The disclosed embodiments are particularly well suited for quickly and accurately determining the concentration of analytes in aqueous systems, including but not limited to boilers, cooling towers, evaporators, gas scrubbers, kilns and desalination units. The methods and reagents compositions described herein are ideally suitable for online analyzer applications. However, they are also suitable for offline, discrete, manual analysis of multiple analytes in water samples.

Free Chlorine+Polymer

In one embodiment, the multi-purpose reagent composition is used to determine both the concentration of free chlorine and anionic polymer corrosion or scale inhibitors in an aqueous sample of industrial water. The reagent composition includes a free chlorine sensitive dye, a pH buffer, a cationic dye, and an organic co-solvent in a single reagent solution. Desirably, the reagent composition does not contain alcohol or a high concentration sulfuric acid. This mild condition makes it possible to blend the composition so the reagent can respond to multiple analytes in the sample.

The free chlorine sensitive dye desirably includes one or more coloring reagents selected from the group consisting of tetraalkyl benzidine compounds. The tetraalkyl benzidine compound is an oxidative chromogenic coloring reagent which has an absorption peak at a wavelength of about 450 to 470 nm in a reaction with free chlorine in an acidic sample, and which colors to a hue within a range of yellow to blue green. U.S. patent application Ser. No. 11/523,021 entitled "Composition for Measuring Residual Chlorine Concentration" discloses suitable tetraalkyl benzidine compounds, including preferred examples N-(2-sulfoethyl)-3,3',5,5'-tetramethylbenzidine; N-(3-sulfopropyl)-3,3',5,5'-tetramethylbenzidine; N-(4-sulfobutyl)-3,3',5,5'-tetramethylbenzidine; N-(2-hydroxy-2-sulfoethyl)-3,3',5,5'-tetramethylbenzidine; N-(2-hydroxy-3-sulfopropyl)-3,3',5,5'-tetramethylbenzidine; N-(2,4-disulfobenzyl)-3,3',5,5'-tetramethylbenzidine; N,N-bis(2-sulfoethyl)-3,3',5,5'-tetramethylbenzidine; N,N-bis(3-sulfopropyl)-3,3',5,5'-tetramethylbenzidine; N,N'-bis (4-sulfobutyl)-3,3',5,5'-tetramethylbenzidine; N,N'-bis(2-hydroxy-2-sulfoethyl)-3,3',5,5'-tetramethylbenzidine; N,N'-bis(2-hydroxy-3-sulfopropyl)-3,3',5,5'-tetramethylbenzidine; N,N'-bis(2,4-disulfobenzyl)-3,3',5,5'-tetramethylbenzidine; and alkali metal salts thereof. Of the compounds, a compound in the form of a sodium salt is particularly preferably used because the compound has high water solubility and is hardly crystallized at normal temperatures.

In one embodiment, the free chlorine sensitive dye is N-(3-sulfopropyl)-3,3',5,5'-tetramethylbenzidine (TMB-PS). The TMB-PS selectively reacts with free chlorine in the presence of chloramines to produce a yellow species with $\lambda max=467$ nm.

The reagent also includes a cationic dye for the determination of an anionic polymer and/or oligomers in the sample. Polymers capable of being detected by the methods disclosed herein include, but are not limited to, water-soluble anionic polymers that contain anionic groups, such as carboxylate, sulfonate, sulfate, phosphonate, phosphate. Examples of the same are polyacrylic acid moiety polymers, polysulfonated polymers, and maleic anhydride polymers. Some specific examples of contemplated anionic polymers are HPS-1. AEC and APES (available from GE Water & Process Technologies of Trevose, Pa.). The cationic dye is chosen from a group of metachromatic dyes, which are dyes that undergo a color change upon interaction with polyionic compounds. The group of dyes from which the cationic dyes are chosen includes, but is not limited to, Dimethyl Methylene Blue (DMMB), Basic Blue 17, New Methylene Blue (NMB), and combinations thereof. One embodiment of the invention calls for the use of 1,9-dimethyl methylene blue (DMMB) as the cationic dye. The cationic dye is added in an effective amount, which amount is generally from about 0.5 to about 3.0 times the molar concentration of the polymer in the assay, in one embodiment, DMMB is added in an amount to obtain 100 ppm of DMMB.

As is known in the art, one factor that needs to be evaluated for each particular polymer is its degree of interaction between that polymer and the dye. This factor can be determined by mapping the absorbance change of a dye as a function of a particular polymer. In order to determine the change in absorbance of a dye composition, an initial absorbance of the dye composition is determined at a set time after mixing the composition at any wavelength in the visible spectrum of 300 to 700 nm. It is possible to quantify the degree of interaction between a particular dye and any polymer, such as, but not limited to, HPS-I.

The reagent composition also includes a pH buffer that does not have any free-chlorine demand. Desirably, weak acids are used as pH buffers to obtain a pH in the range of 2.85 to 4.5. Suitable weak acids are acetic acid and citric acid; however, other acids such as phthalic acid, oxalic acid, succinic acid may also be used. For example, DMMB precipitates quickly from the assay solution upon addition of a polymer. However, it has been found that DMMB is stable in acetate and citric buffer in the pH range of 2.85 to 4.5, even if a stabilizing agent is not added into the DMMB-buffer mixture. Therefore, addition of a stabilizing agent is not necessary for online application where the reagent and sample are brought to mix by pumps and the distance and time between the mixing point and the measurement point are controlled and reproducible.

The reagent may also contain a masking agent for the masking of surfactants or other chemical species that may interfere with the results that may be present with the polymers and/or oligomers. It is known to add stabilizing agents to the buffer to assists with solving the issue of precipitation and assay instability. Anionic surfactants or co-existing polymer can be effectively masked by including a masking agent in the multifunctional buffer. By including such a masking agent, the reading of the polymer concentration is more accurate. An example of an anionic surfactant that can be masked by adding a cationic surfactant to the aqueous system is dodecylbenzene sulfonate. The masking agent is added in an amount of from 20 ppm to about 3000 ppm. Masking agents include, but are not limited to, bivalent manganese salt, ferrous salt, calcium salts, zinc salts, quaternary amine surfactant, or combinations thereof. In one embodiment, the masking agent is 2500 ppm calcium chloride dehydrate.

The reagent composition also includes an organic co-solvent. The organic co-solvent is desirable selected from the group of water-soluble ketones, acetone, NMP, ethylene glycol, and methanol. When TMB-PS and DMMB were mixed in a pH=3.4 citric buffer, a cloudy solution was formed and filtering the cloudy mixture through a 0.2 ml filter resulted a solution essentially free of DMMB and TMB-PS. This is presumably because the sulfonic acid group from TMB-PS forms an ion pair with the positive quaternary amine cation from DMMB. It was found that adding 1 ml acetone into 3 ml of the cloudy mixture produces a homogenous solution. Filtering through the 0.2 μm filter confirmed that the new composition containing 25% acetone is essentially free of particulates.

Absorbance, as used herein, is defined according to the Lambert-Beer Law in Equation 1 as follows:

$$A=abc \qquad \text{(Eq. 1)}$$

where:
A=absorbance;
a=absorptivity of the dye;
b=light path length; and
c=concentration of the colored substance.

Each cationic dye used will have a maximum absorbance within the 300 to 1000 nm range, and it is desirable to measure absorbance at a wavelength within the range of maximum absorbance. Absorbance may be measured using any suitable device known in the art to measure absorbance. Such suitable devices include, but are not limited to, calorimeters, spectrophotometers, color-wheels, and other types of known color-comparative measuring tools. One embodiment provides for measurements of optical response performed using an optical system that includes a white light source (such as a Tungsten lamp available from Ocean Optics, Inc. of Dunedin, Fla.) and a portable spectrometer (such as Model ST2000 available from Ocean Optics, Inc. of Dunedin, Fla.). Desirably, the spectrometer used covers the spectral range from about 250 nm to about 1100 nm.

The method includes the use of predetermined calibration curves for optimal efficiency and effectiveness. In order to determine the concentration or amount of available anionic polymer in an industrial water system, it is first necessary to generate a calibration curve for each polymer of interest. Calibration curves are generated by preparing various samples of water containing known amounts of polymer, making an appropriate reagent composition and measuring the absorbance of the sample using the reagent composition. In one embodiment of this invention, absorbance is being reported as absorbance difference. Absorbance difference is the difference between the absorbance of the reagent composition by itself and the absorbance of the mixture of reagent composition and the sample of water being tested. The calibration curve is then a plot of this absorbance difference versus the known concentration of the polymer in the sample. Once created, the calibration curve can be used to tell how much polymer is present in a sample by comparing the measured absorbance difference of the sample with the curve and reading the amount of polymer present off the curve.

EXAMPLE 1

Free chlorine concentration in tap water is determined using a TMB-PS solution as shown in FIG. 1. The TMB-PS solution used contained 175 ppm TMB-PS and 0.1M, pH=3.4 citric acid/sodium citrate buffer. Total chlorine concentration determined using a TMB solution is also included in FIG. 1. During the test, the tap water contained 0.05 to 0.15 ppm chlorine and 1.5 to 1.9 ppm total chlorine, both confirmed by independent free chlorine analysis methods. The total chlorine is presumably monochlorame. This example demonstrates that TMB-PS responds selectively to free chlorine even at a large excess of monochlorame.

EXAMPLE 2

Figure 2:
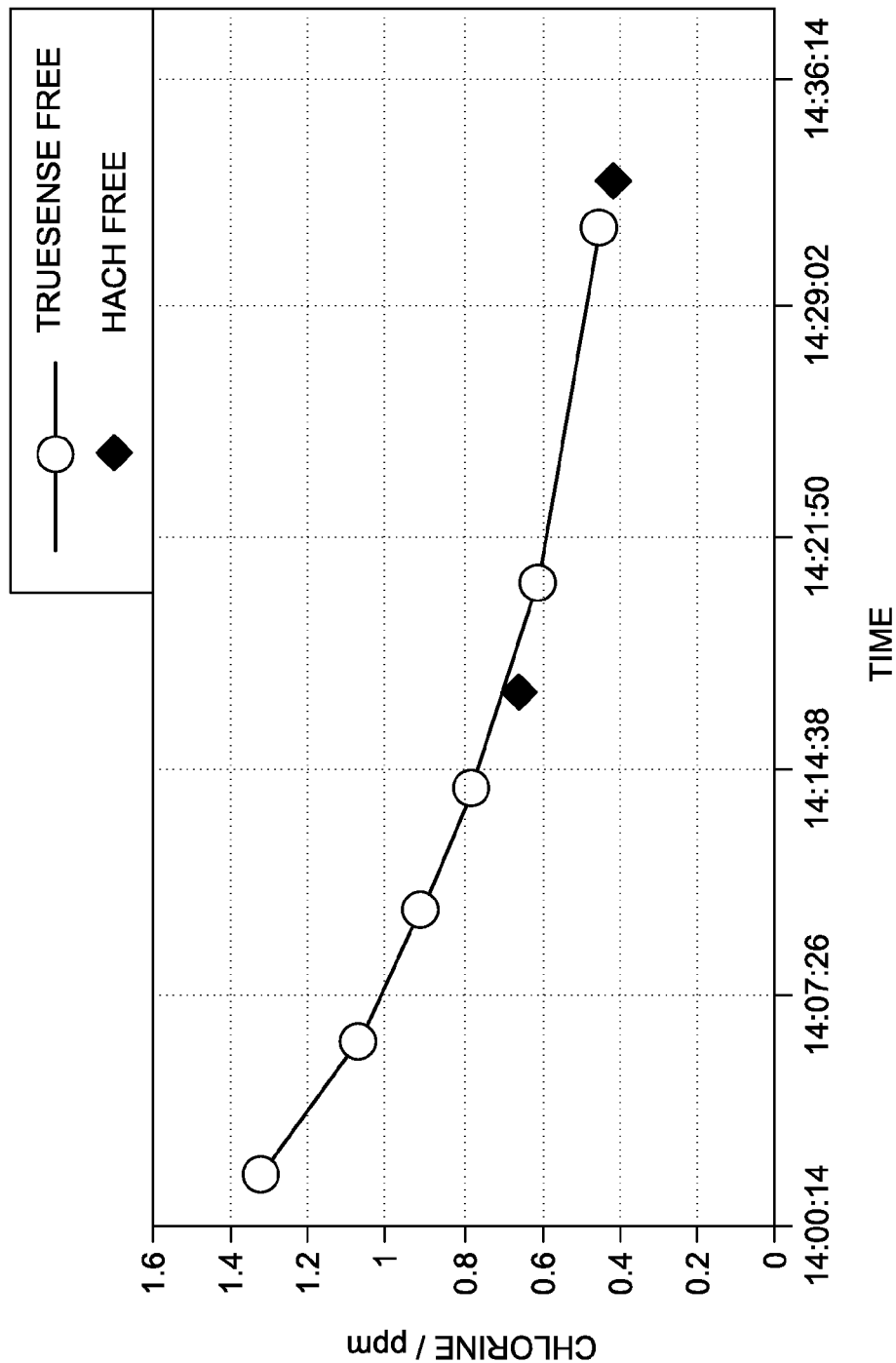
FIG. 2 is a graph showing free chlorine decay in the presence of ammonium chloride.

A 1.57 ppm chlorine solution was prepared by adding 5 ml 63.4 ppm chlorine standard solution purchased from Hach into a 200 ml volumetric flask. 0.5 ml 100 ppm ammonium chloride solution was added to the flask and deionized water was added to the 200 ml mark. Free chlorine concentration in this solution was analyzed immediately. The free chlorine decay caused by ammonium ion was monitored and is shown in FIG. 2 along with the five chlorine concentration measured by the Hach DPD method. This example shows that TMB-PS in pH 3.4 citric buffer responds selectively to free chlorine, and chloramine does not interfere with the free chlorine analysis.

EXAMPLE 3

A 75 g solution containing 175 ppm TMB-PS and 160 ppm DMMB was prepared in 0.1 M, pH=3.4 citric buffer. The solution was cloudy. The final all-in-one reagent was prepared by adding 25 g acetone to the cloudy solution.

Figure 3:
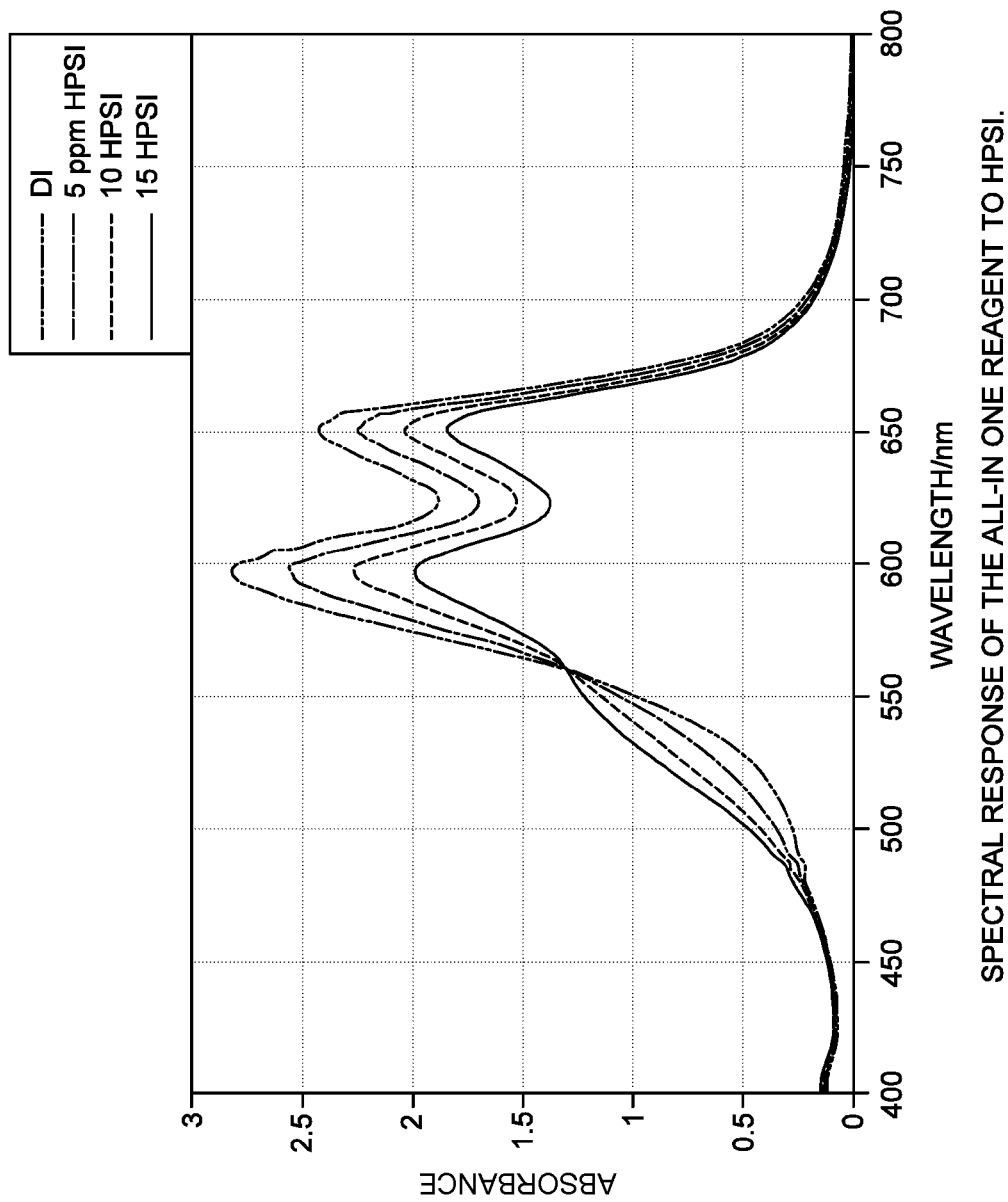
FIG. 3 is a graph showing spectral response of the multi-purpose reagent to anionic polymer.
Figure 4:
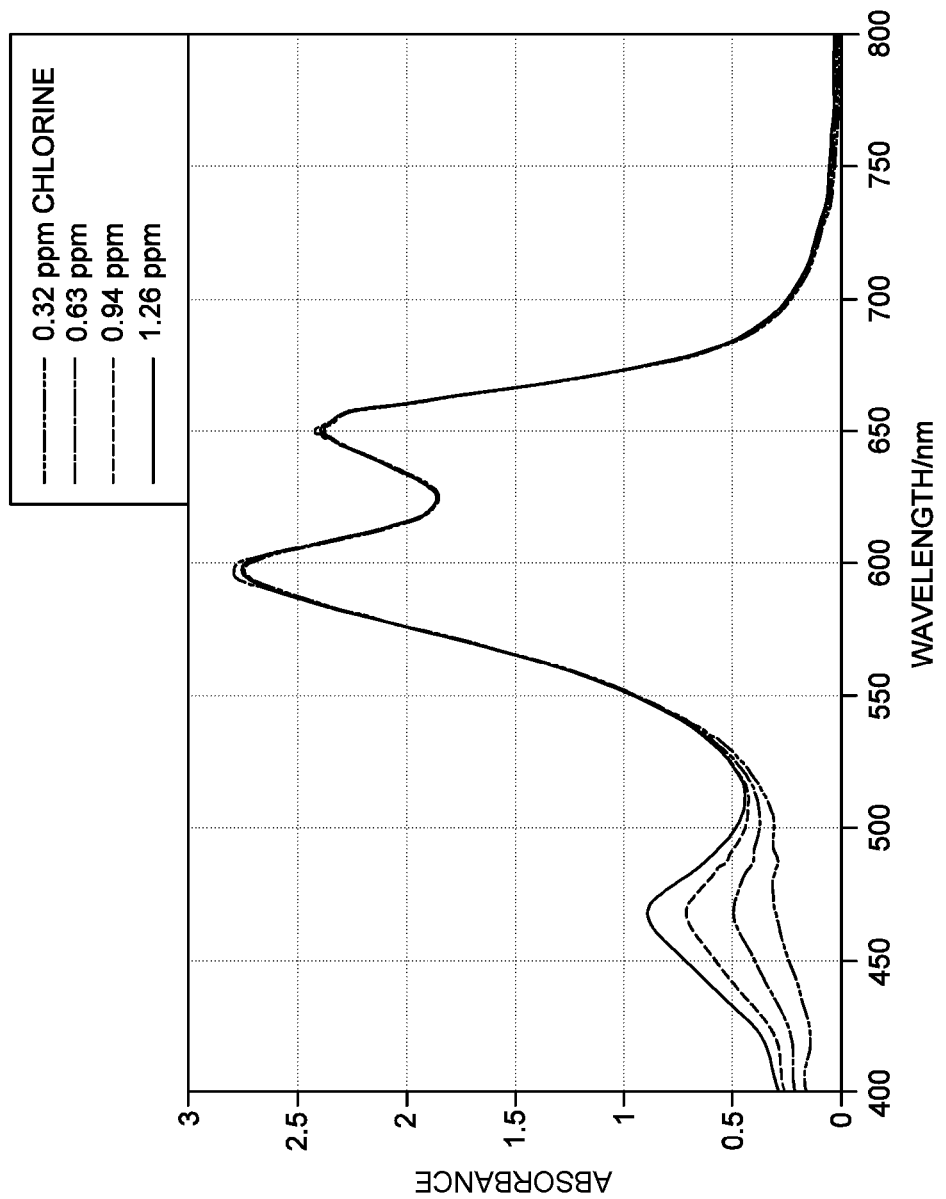
FIG. 4 is a graph showing spectral response of the multi-purpose reagent to free chlorine.
Figure 5:
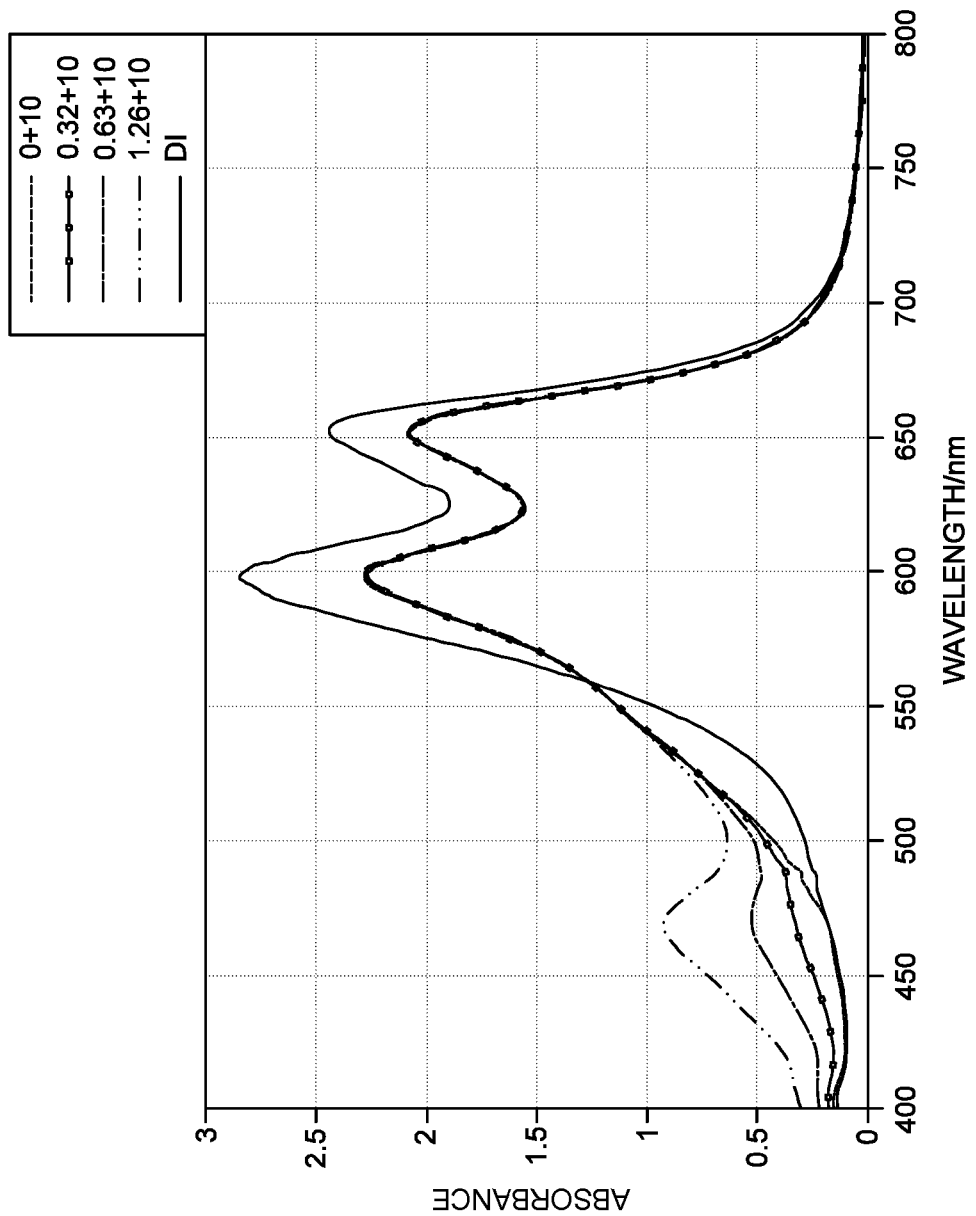
FIG. 5 is a graph showing spectral response of the multi-purpose reagent to chlorine/HPSI mixtures.

FIGS. 3 and 4 show the response of the all-in-one reagent to free chlorine and HPSI respectively. It is clear that the response of TMB-PS to free chlorine is not affected by the presence of DMMB, and the response of DMMB to HPSI is not affected by TMB-PS. FIG. 5 shows the response of the all-in-one reagent to solutions containing 10 ppm HPSI and 0.0 to 1.26 ppm free chlorine. It is apparent that the 468 nm peak of TMB-PS is essential free of interference from the 520 nm band of the DMMB-HPSI complex. The spectral region between 535 nm and 700 nm of the DMMB-HPSI complex is not affected by TMB-PS's 468 nm peak. However, the 468 nm peak is overlapped with the 520 nm shoulder of the DUMB-HPSI complex. We found that a multivariate calibration equation using absorbance values at 468 nm, 525 nm, and 634 nm is adequate to predict HPSI concentration in a free chlorine/HPSI mixture.

Figure 6:
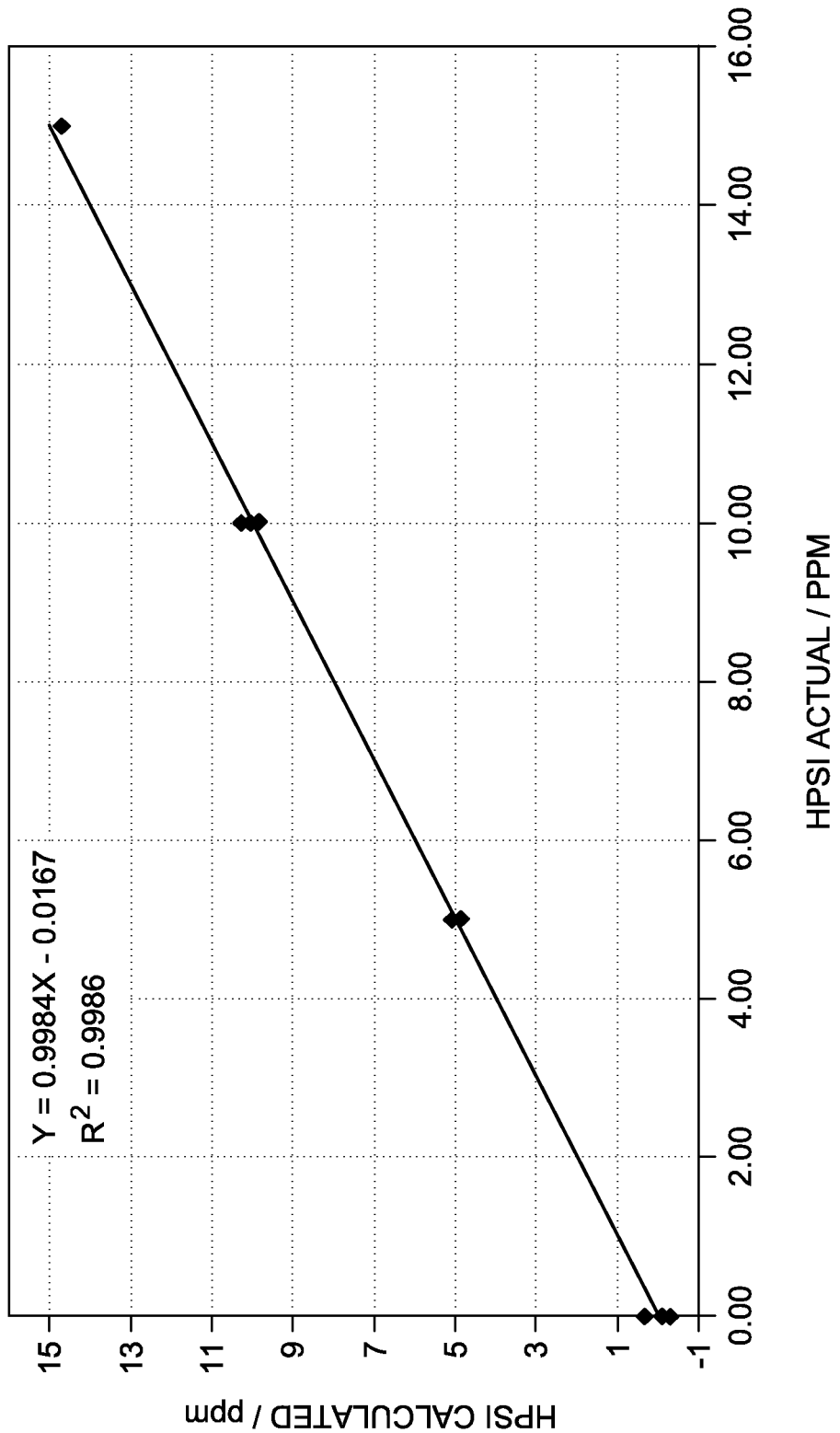
FIG. 6 is a graph showing the multivariate calibration equation representing the HPS-I concentration.

FIG. 6 shows the predicted concentration from Equation 2 as follows:

$$HPSI/ppm = 17.2 - 1.18 A_{467} + 19.4 A_{525} - 12.8 A_{634} \quad \text{(Eq. 2)}$$

where $A_{467}$, $A_{525}$, and $A_{634}$ are absorbance value at 467, 525, and 634 nm respectively.

Figure 7:
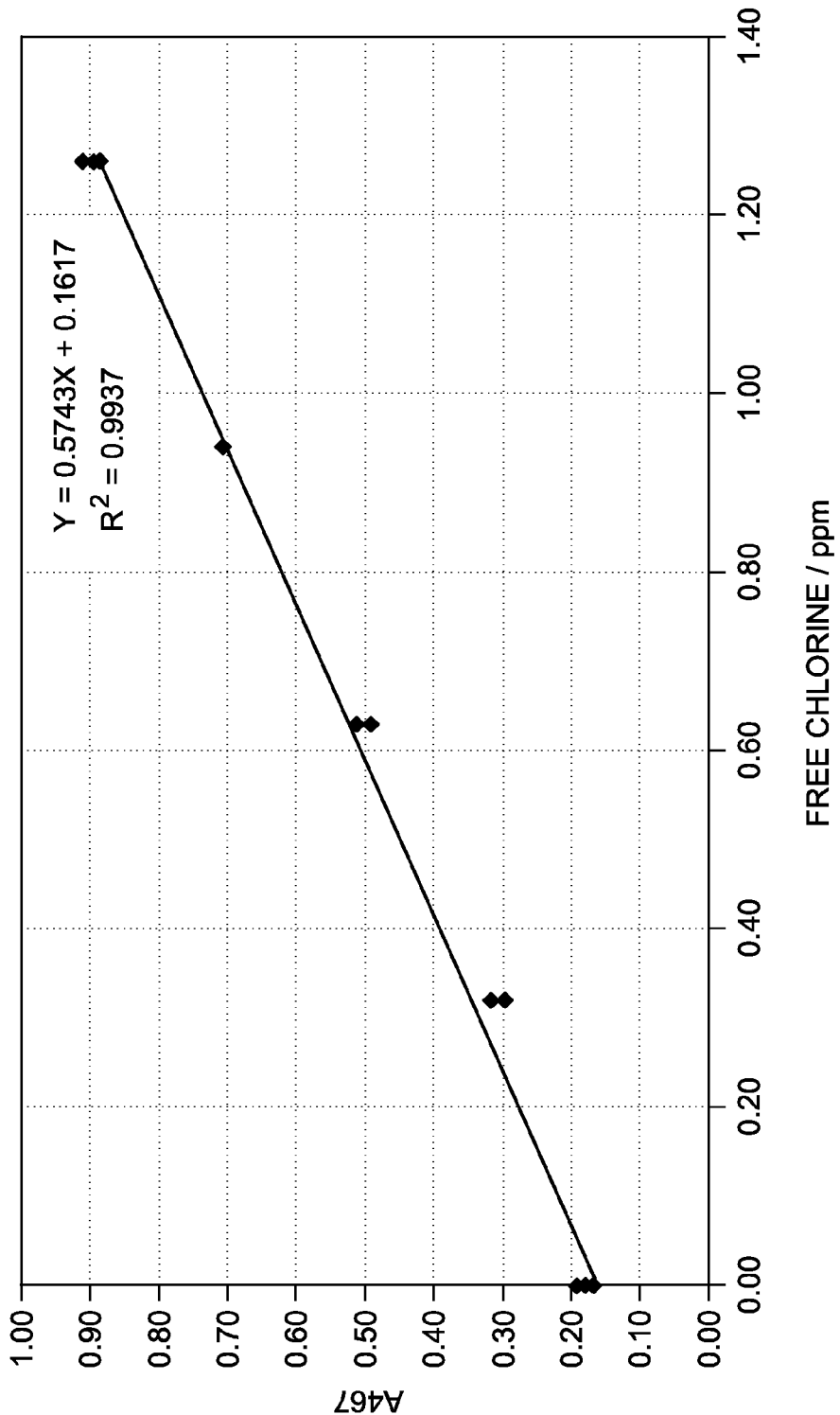
FIG. 7 is a graph showing absorbance at 467 nm as a function of chlorine concentration.

Since the TMN-PS response at 468 nm is essentially free of interference from DMMB-HPSI complex, absorbance value at 460 nm alone can be used to calibrate TMB-PS's response to free chlorine, as shown in FIG. 7.

Absorbance values measured at 467 nm, 525 nm, 580 nm, and 634 nm are listed in Table 1,

TABLE 1

| Chlorine/ppm | HPSI/ppm | 467 nm | 525 nm | 580 nm | 634 nm |
|---|---|---|---|---|---|
| 0.00 | 0.00 | 0.1678 | 0.4641 | 2.2928 | 2.0549 |
| 0.00 | 5.00 | 0.1689 | 0.6215 | 2.0681 | 1.8737 |
| 0.00 | 10.00 | 0.1804 | 0.7654 | 1.8391 | 1.6877 |
| 0.00 | 15.00 | 0.1897 | 0.8895 | 1.6542 | 1.5266 |
| 0.32 | 0.00 | 0.2960 | 0.4565 | 2.2382 | 2.0195 |
| 0.63 | 0.00 | 0.4910 | 0.4857 | 2.2748 | 2.0393 |
| 0.94 | 0.00 | 0.7068 | 0.5120 | 2.2368 | 2.0279 |
| 1.26 | 0.00 | 0.8866 | 0.5084 | 2.2584 | 2.0380 |
| 0.00 | 10.00 | 0.1804 | 0.7654 | 1.8391 | 1.6877 |
| 0.32 | 10.00 | 0.3177 | 0.7649 | 1.8181 | 1.7020 |
| 0.63 | 10.00 | 0.5121 | 0.7801 | 1.8044 | 1.6953 |
| 1.26 | 10.00 | 0.9114 | 0.8125 | 1.8187 | 1.7220 |
| 1.26 | 5.00 | 0.8961 | 0.6746 | 2.0474 | 1.9009 |

FIG. 6 shows that the multivariate calibration equation accurately represents the HPSI concentration regardless of chlorine concentration in the standard solution. Note that five points are included for 0 and 10 ppm HPSI standard solutions, which contain five different chlorine concentrations.

Free Chlorine+pH

Another embodiment of the invention is a reagent composition and method for simultaneously determining free chlorine and pH in a sample. This reagent composition comprises a free chlorine sensitive dye and pH indicator.

The free chlorine sensitive dye is selected from the group of infrared dyes. The pH indicator is a colorimetric pH indicator. Desirably, the pH indicator is a fluorescence pH indicator. Several IR dyes at the pH range of 6.5-10.5, such as IR-783, selectively react with free chlorine. The free chlorine concentration is proportional to the decrease of absorbance at near infrared wavelength 780 nm. The extremely high molar absorbability (around $2 \times 10^5$ $M^{-1}$ $cm^{-1}$) of IR dyes enables free chlorine to be detected at the ultra-low range. The response of IR dyes to free chlorine is dependent on pH. Traditional free chlorine detection methods usually use a pH buffer to control sample pH.

Unlike the traditional methods, this embodiment uses a reagent composition containing a free chlorine tolerant pH indicator and an IR dye in a solvent mixture. In one embodiment, the solvent mixture contains 25% (w/w) methanol and 75% (w/w) ethylene glycol; however, any solvent, and/or solvent mixture that dissolves the free chlorine sensitive dye and the indicator could be used. Desirably, the solvent should not react with free chlorine and affect pH sample. Therefore, amine or an acid solvent should not be used. The solvent should dissolve the dyes well without substantial precipitations. It is desirable to have a solvent to dissolve both dyes and also stabilize the dye mixture, thus increasing the shelf-life of the dye mixture. It has been found that the dye mixture of IR-783 and cresol red is much more stable in ethylene glycol than in water. The solvent mixture of methanol and ethylene glycol is desirable because it decreases the viscosity of the dye mixture enabling the mixture to be easily and accurately pumped. Suitable IR dyes include IR-783, IR-780, IR-775, IR-746, Pinacyanol chloride (CAS: 2768-90-3). Suitable free chlorine tolerant pH indicators include cresol red and phenol red, phenolphthalein, thymol blue, and O-cresolphthalein. This composite reagent formulation of these IR dyes and pH indicators allows the mixed reagent to be very stable and reduces cross interference during and free chlorine detection, thereby enabling free chorine and pH to be measured simultaneously. A multivariate calibration equation is used to determine the free chlorine concentration. Since the pH response at 575 nm is essentially free of interference from IR dyes, absorbance value at 575 nm alone can be used to calibrate pH response as described below.

EXAMPLE 4

The composite reagent composition for free chlorine and pH measurement was made by mixing of 10 mg IR-783 and 10 mg cresol red sodium salt in a solvent mixture containing 25% (w/w) methanol and 75% (w/w) ethylene glycol. Calibration solutions were made from synthetic cooling water with different pH and free chlorine concentration. The pH and free chlorine concentration were analyzed by standard methods. A 2 ml standard solution was mixed with 50 µl reagent composition for 20 seconds; the spectra were recorded by using a UV-Vis spectrophotometer.

Figure 8:
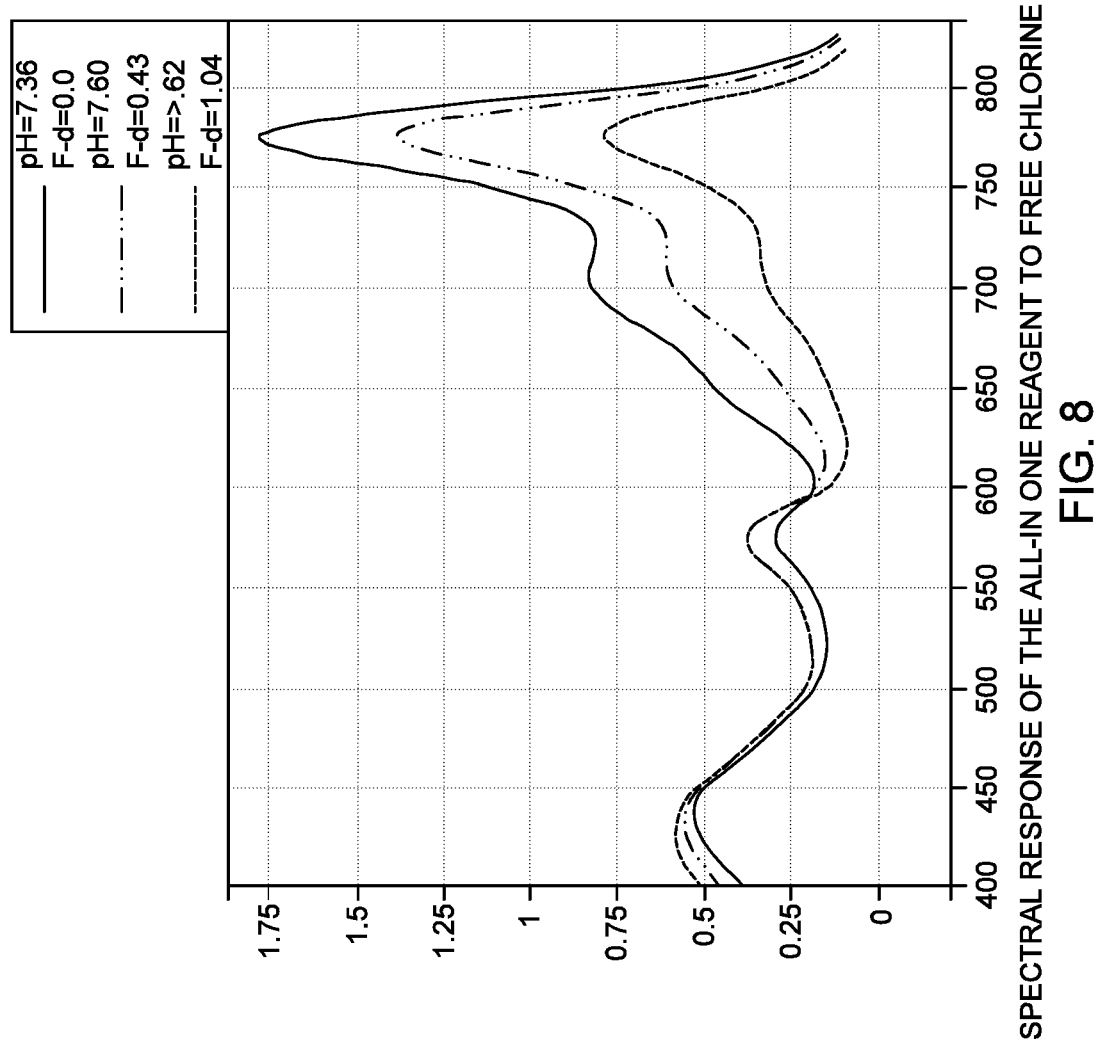
FIG. 8 is a graph showing spectral response of the multi-purpose reagent to free chlorine at pH around 7.6.
Figure 9:
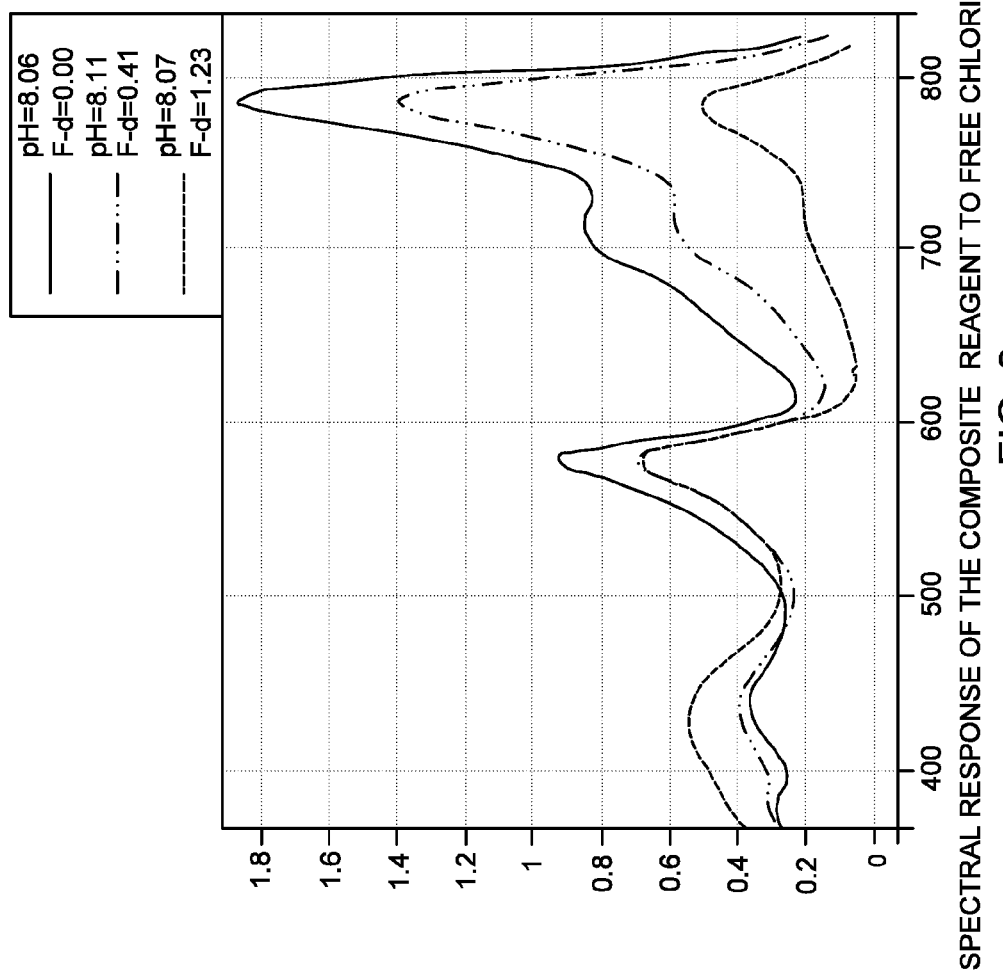
FIG. 9 is a graph showing spectral response of the multi-purpose reagent to free chlorine at pH around 8.0.
Figure 10:
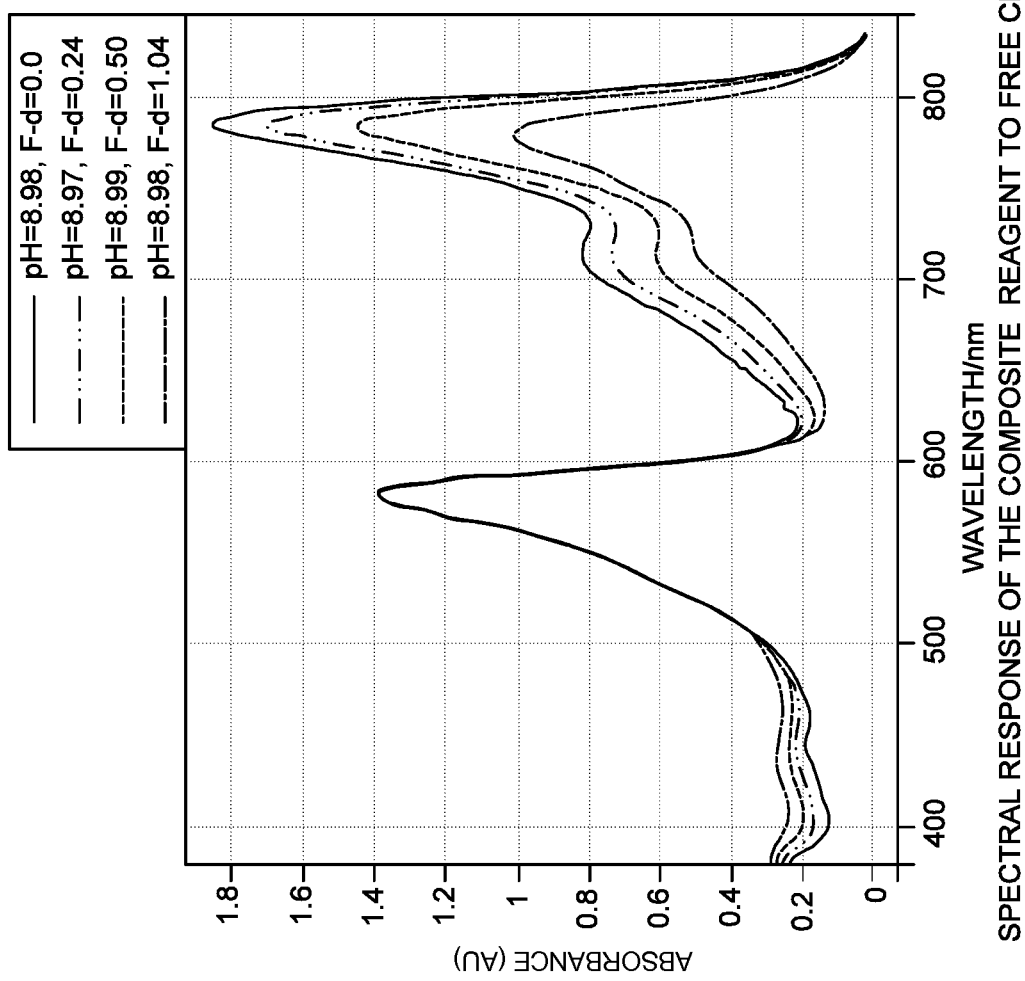
FIG. 10 is a graph showing spectral response of the multi-purpose reagent to free chlorine at pH around 9.0.

FIGS. 8, 9, and 10 show the response of the reagent to 0.0 to 1.0 ppm free chlorine at pH 7.6, 8.0, and 9.0. It is clearly that the response of free chlorine is not affected by the presence of pH indicator cresol red sodium salt and the response of pH is not significant affected by the presence of IR 783.

Figure 11:
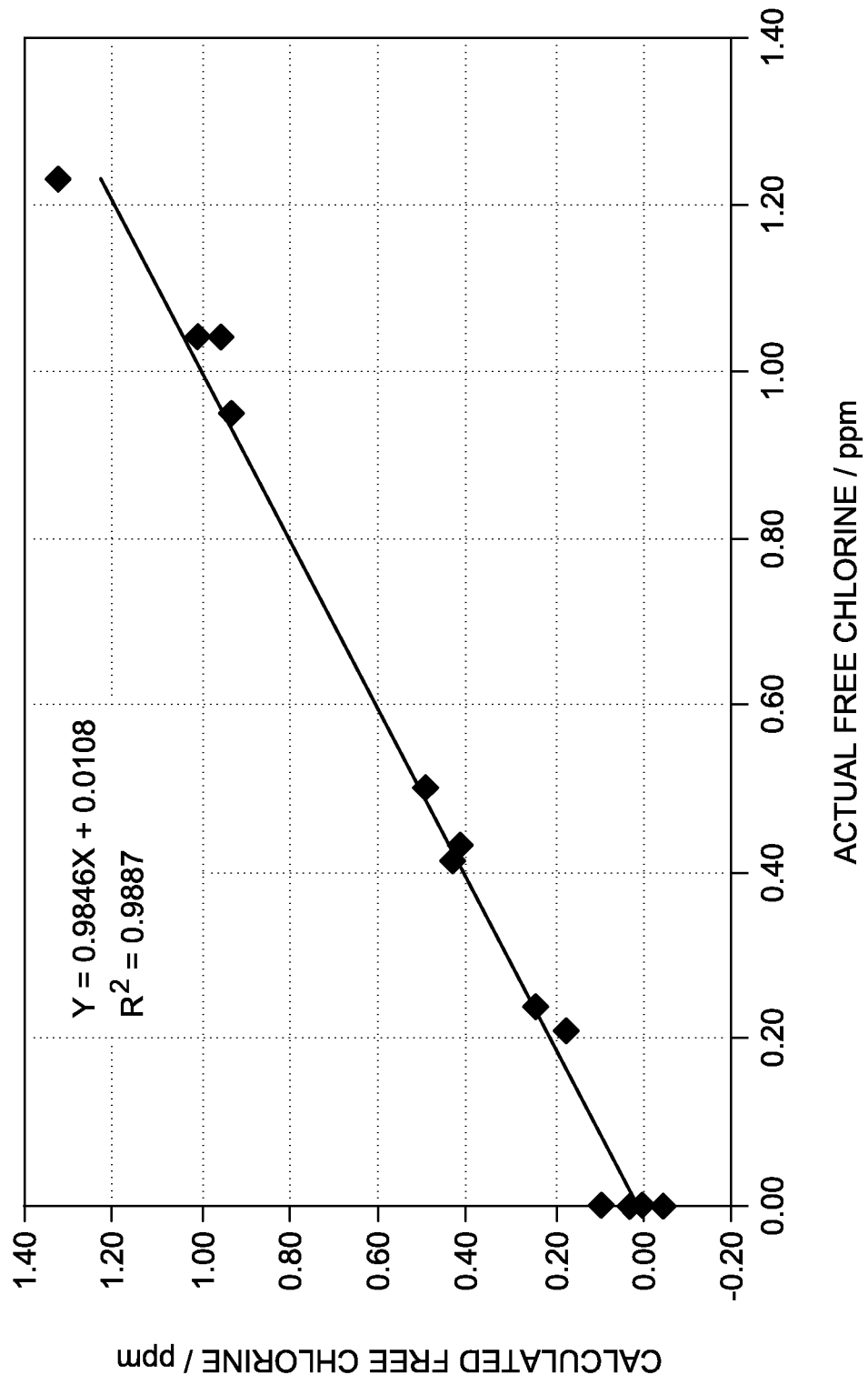
FIG. 11 is a graph showing the multivariate calibration equation representing free chlorine concentration.

It was found that a multivariate calibration equation using absorbance values at 575 nm and 775 nm is adequate to predict free chlorine concentration. FIG. 11 shows the predicted free chlorine concentration from the following equation:

$$F\text{—}Cl/ppm = 1.71 + 0.180 * A_{575\,nm} - 1.00 * A_{775\,nm} \quad \text{(Eq. 3)}$$

Absorbance values measured at 575 nm, 775 nm, plus actual pH, F—Cl/ppm and calculated pH, F—Cl/ppm were listed in Table 2,

TABLE 2

| 575 nm | 775 nm | F—Cl | pH | F—Cl Cal. | pH Cal. |
|---|---|---|---|---|---|
| 1.38 | 1.86 | 0.00 | 8.98 | 0.10 | 8.95 |
| 1.39 | 1.71 | 0.24 | 8.97 | 0.25 | 8.96 |
| 1.37 | 1.46 | 0.50 | 8.99 | 0.50 | 8.94 |
| 1.39 | 1.00 | 1.04 | 8.98 | 0.96 | 8.96 |
| 0.92 | 1.87 | 0.00 | 8.06 | 0.01 | 8.32 |
| 0.69 | 1.40 | 0.41 | 8.11 | 0.44 | 8.01 |
| 0.68 | 0.51 | 1.23 | 8.07 | 1.32 | 7.99 |
| 0.68 | 0.90 | 0.95 | 8.07 | 0.93 | 8.00 |

TABLE 2-continued

| 575 nm | 775 nm | F—Cl | pH | F—Cl Cal. | pH Cal. |
|---|---|---|---|---|---|
| 0.82 | 1.90 | 0.00 | 8.06 | 0.00 | 8.19 |
| 0.77 | 1.67 | 0.21 | 8.16 | 0.17 | 8.11 |
| 0.29 | 1.75 | 0.00 | 7.36 | 0.01 | 7.45 |
| 0.36 | 0.76 | 1.04 | 7.62 | 1.01 | 7.55 |
| 0.37 | 1.36 | 0.43 | 7.60 | 0.42 | 7.56 |
| 0.46 | 1.76 | 0.00 | 7.67 | 0.03 | 7.68 |

Figure 12:
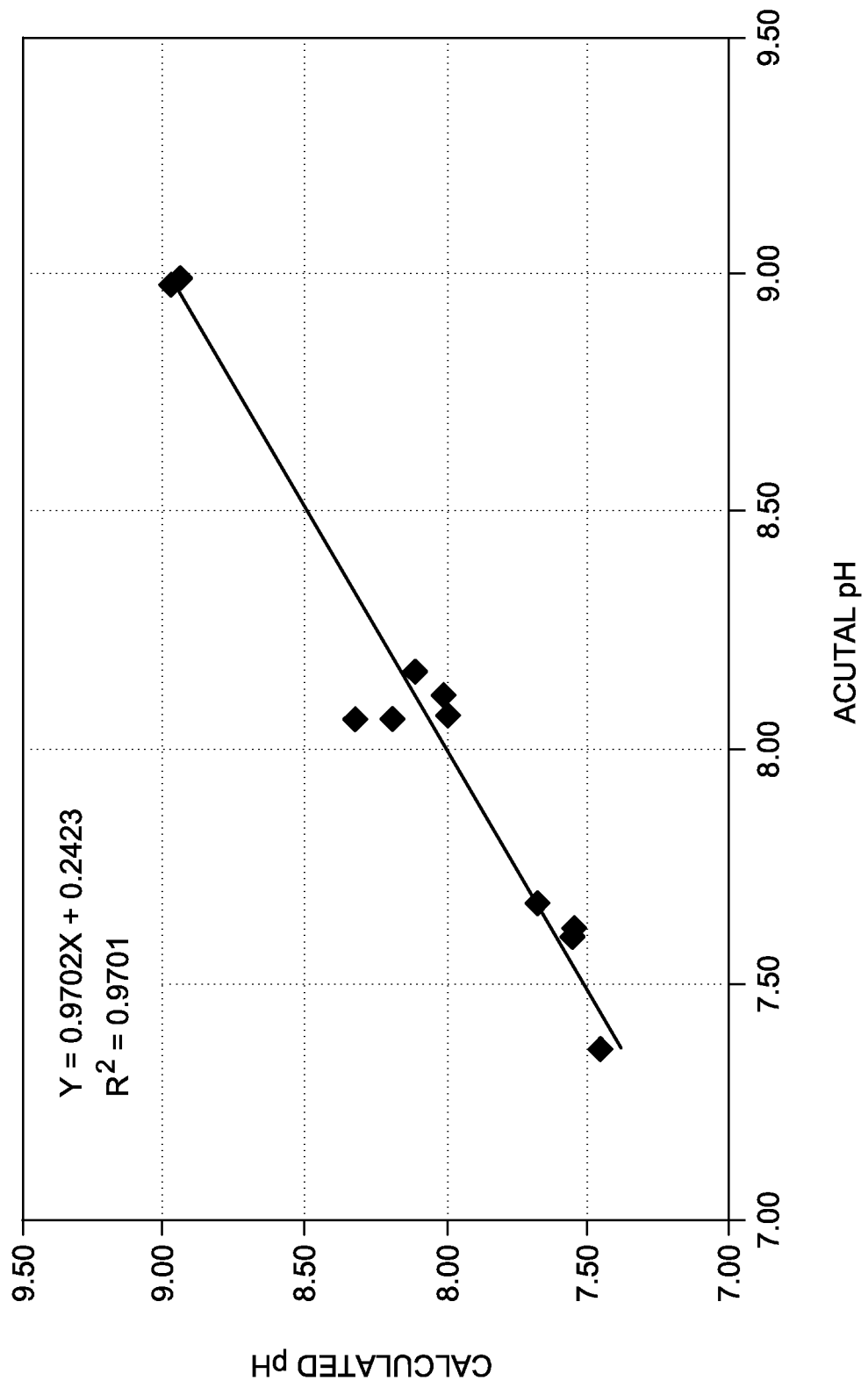
FIG. 12 is a graph showing the multivariate calibration equation representing pH.

FIG. 11 shows that the multivariate calibration equation accurately represents the free chlorine concentration in the standard solutions. Since the pH response at 575 nm is essentially free of interference from IR dyes, absorbance value at 575 nm alone can be used to calibrate pH response as shown in FIG. 12 according to the following equation:

$$pH = 7.06 + 1.37 * A_{575\,nm} \quad \text{(Eq. 3)}$$

HPSI+PO4

Another embodiment of the invention is a reagent composition and method of determining phosphate concentration and anionic polymer concentration in a water sample. In one embodiment, the anionic polymer is measured by mixing the sample with the polymer-measuring reagent as described above. High range phosphate is measured by mixing the sample with a phosphate reagent alone, while the lower range phosphate is measured by mixing the sample with the phosphate reagent and the reagent used to measure the anionic polymer mixed together as will be described below. This mixing sequence can be easily recognized in any online flow analysis system.

Vanadomolybdate has been widely used for the determination of phosphate concentration in water samples. The advantage of this method is that only a single reagent composition is needed to cover the phosphate concentration in a large range (0 to 50 ppm). The disadvantages include high strong acid concentration, low sensitivity, and the need of using near IN light sources, which make the method sensitive to interference of yellow background color, which is common for nature water samples. In Example 2 above, it was demonstrated that an anionic polymer such as HPS-I from GE Water & Process Technologies could be determined from a single reagent composition containing both the buffer and the dye. With a careful selection of the reagent pH and concentration, vanadomolybdate reagent and the cationic dye in the reagent designed for anionic polymer determination can be used to analyze phosphate at the range of 1 to 3 ppm. Accordingly, an online wet chemistry procedure can be designed to measure anionic polymer and phosphate in the range of 0 to 40 ppm with great accuracy for the 0 to 3 ppm range.

EXAMPLE 5

Figure 13:
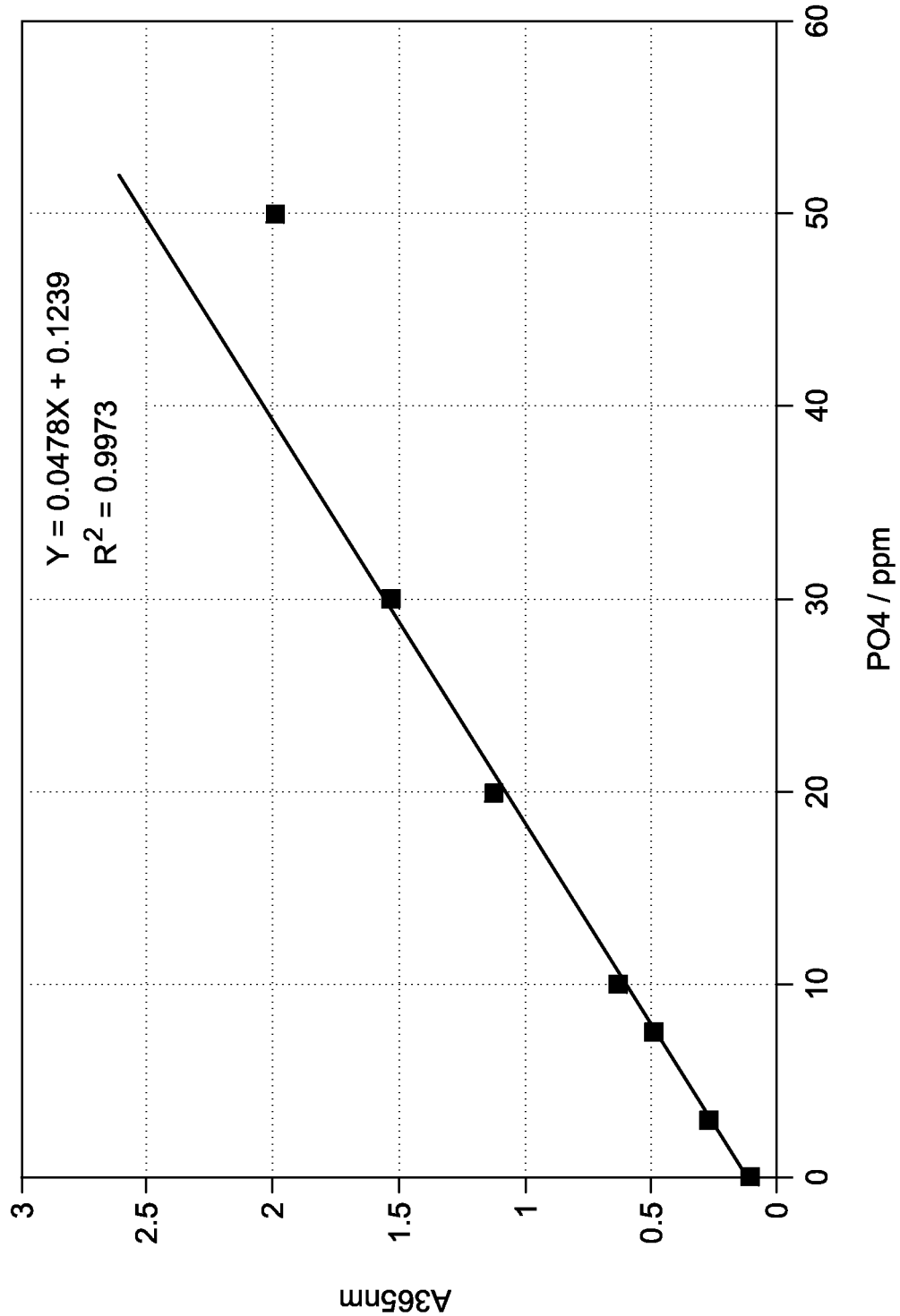
FIG. 13 is a graph showing a calibration curve of a vanadomolybdate method for phosphate determination.

FIG. 13 shows a calibration curve of the vanadomolybdate method for phosphate determination. The vanadomolybdate reagent pH is adjusted using sulfuric acid and sodium hydroxide to pH 1.4. The reagent composition contains enough vanadomolybdate for 40 ppm orthophosphate when the reagent to sample ratio is 3/1. The absorbance shown in FIG. 13 was measured at 365 nm from a 10 mm quartz cell. From the data presented in FIG. 13, the sensitivity of the method at 365 nm is 0.05 au/ppm PO4.

Figure 14:
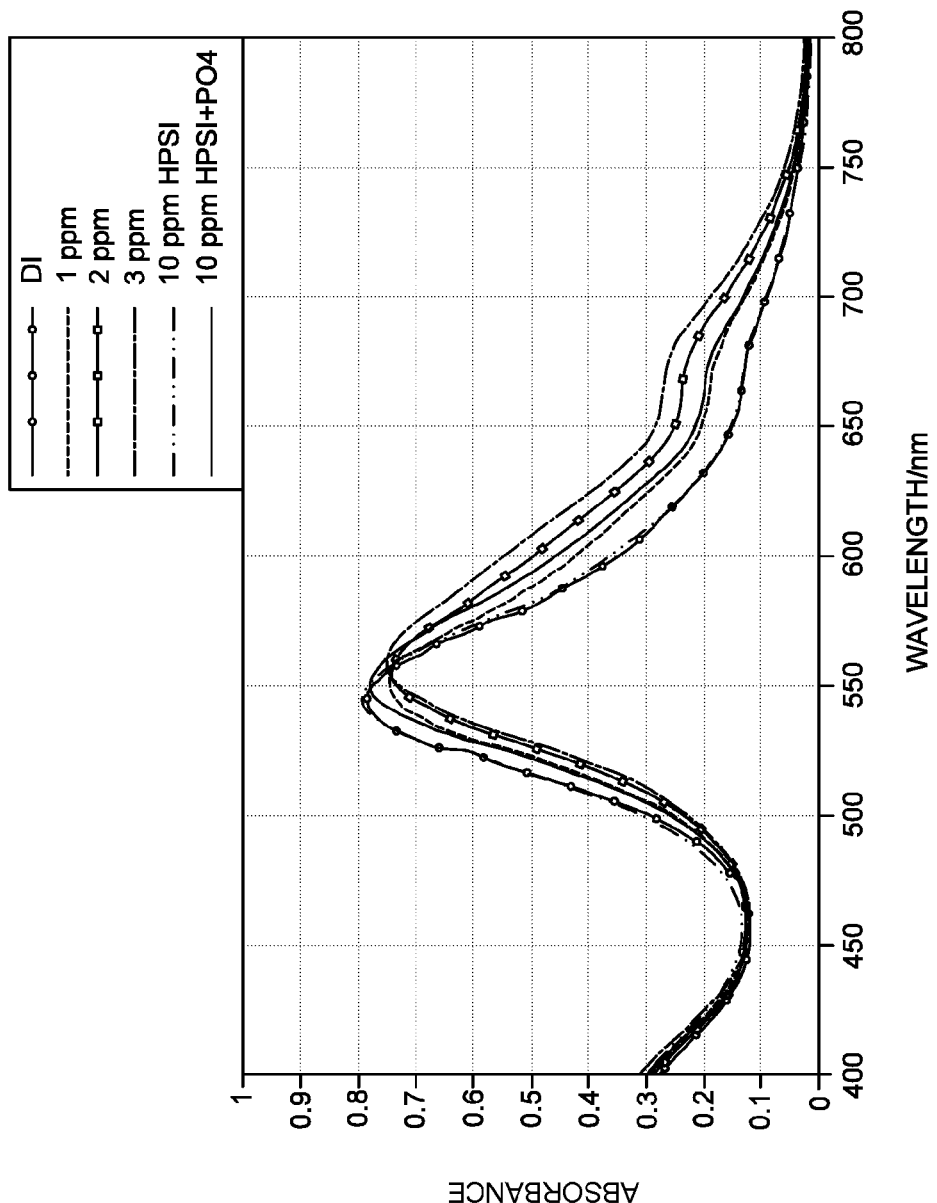
FIG. 14 is a graph showing results obtained from mixing a sample containing phosphate, HPSI, vanadomolybdate and multi-purpose reagent for measuring HPSI.
Figure 15:
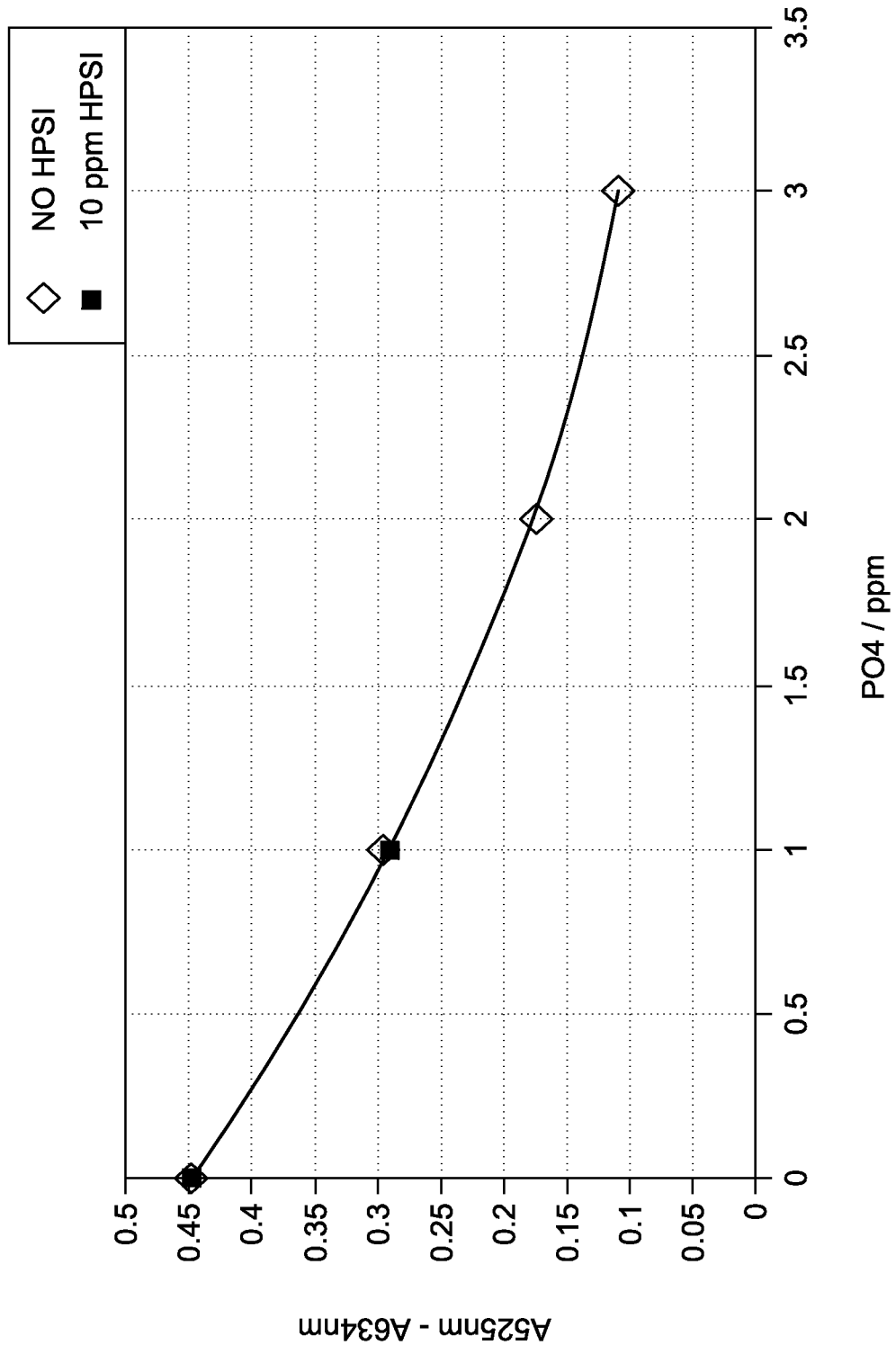
FIG. 15 is a graph showing measurements of lower range phosphate.

FIG. 14 shows the results obtained from mixing three parts of sample containing phosphate and one part of the vanadomolybdate that is used for the results shown in FIG. 13, and one part of the reagent used to determine HPS-I. From the results shown in FIG. 14, it can be seen that the concentration of HPS-I does not interfere with the phosphate determination. Additionally, it was determined that the sensitivity is at least seven times of that of the traditional vanadomolybdate method as shown in FIG. 13. Therefore, HPS-I is measure by mixing the sample with the multi-purpose reagent alone, the high range phosphate is measured by mixing the sample with the vanadomolybdate alone, and the lower range phosphate is measured by mixing the sample with the vanadomolybdate and the all-in-one together. This mixing, sequence can be easily recognized in any online flow analysis system.

pH Composition as a Phosphate Standard

Another embodiment of the invention is a multi-functional reagent composition that can be used for determining at least one analyte when it is used alone and has other functionality to assist the determination of other analytes in an online analyzer system comprising an analyte-sensitive reagent, solvent, and ancillary reagent. In one embodiment, the reagent composition functions to act as a reagent for the determination of another analyte along with a second reagent composition. In another embodiment, the reagent composition functions to act as a buffer for the determination of another analyte along with a second reagent composition. In another embodiment, the reagent composition functions to act as a cleaning agent to clean the residual left from the analysis of other analytes. In another embodiment, the reagent composition functions to act as a calibration solution that can be to calibrate the reagents in said online system. The ancillary reagent is desirably selected from the group including an acid, a surfactant, a buffer, or a complexing agent such as EDTA.

EXAMPLE 6

A 2 ml phosphate standard solution was mixed with 1 ml vanadomolybdate solution in a 10 mm quartz cuvette. Absorbance at 365 nm was measured. A calibration curve was produced. A second set of absorbance values at 355 nm were measured from five phosphate standard solutions. The phosphate concentrations of these five solutions were calculated according to the calibration obtained at 365 nm. The deviations of calculated values from the theoretical values are listed below.

TABLE 3

| $PO_4$ ppm (theoretical) | Abs at 365 nm | $PO_4$ calculated based on calibration curve generated from abs at 365 nm | Deviation from the true value |
| --- | --- | --- | --- |
| 0 | 0.1953 | 1.11 | −1.11 |
| 3 | 0.3422 | 4.57 | −1.57 |
| 10 | 0.7048 | 13.12 | −3.12 |
| 20 | 1.2232 | 25.35 | −5.35 |
| 30 | 1.6367 | 35.10 | −5.10 |

It is clear that if a photometer has some error in wavelength, the phosphate concentration measured based on a global calibration curve is subject to error. We demonstrate in this example that this type of error can be reduced by online calibration from a reagent composition containing phosphate.

A cresol red solution containing 5 ppm phosphate was prepared. Because phosphate concentration in the cresol red is insignificant, it can be used to measure pH. Absorbance values at 360, 362, 365, and 367 nm were measured after 2 ml phosphate standard solution and 1 ml vanadomolybdate, and 1 ml cresol red solution are mixed in a 10 mm cuvette. The measurement was carried out for each phosphate standard solution. Absorbance values at these wavelengths were also measured in the absence of cresol right solution. Absorbance values from the above measurements were fitted to a two-variable equation:

$$PO_4 = 26.84 - 78.06\,A_{cresol} + 96.21\,A$$

where:

$A_{cresol}$ is absorbance measured when the sample, vanadomolybdate, and cresol red solutions are mixed, and A is absorbance measured when sample and vanadomolybdate were mixed.

Note that wavelength information is absent from the calibration equation. Therefore, absorbance values can be measured with the same optical and fluidic setup with and without cresol red addition. Phosphate concentrations calculated from the above calibration equation are listed in Table 4. It is clear that absorbance measurement from the phosphate containing pH reagent can be used to reduce variations caused by variation in photometer wavelength. To those skilled in the art, this method demonstrated in this example can be used to correct other types of errors in the photometric measurement.

TABLE 4

| $PO_4$ ppm (theoretical) | Abs at 360 nm (sample + cresol red + VMo reagent) | Abs at 360 nm (sample + VMo reagent) | $PO_4$ calculated based on two variable calibration equation | Deviation from the true value |
| --- | --- | --- | --- | --- |
| 0 | 0.5943 | 0.1953 | −0.76 | 0.76 |
| 3 | 0.7301 | 0.3422 | 2.77 | 0.23 |
| 10 | 1.0891 | 0.7048 | 9.63 | 0.37 |
| 20 | 1.5576 | 1.2232 | 22.93 | −2.93 |
| 30 | 1.9660 | 1.6367 | 30.84 | −0.84 |

It can be seen that varying reagents/sample mixing sequence enables multiple analytes to be measured simultaneously or sequentially. With the understanding of the discovered underline principles, we have demonstrated that the following combinations of analytes, which are significant to cooling tower monitoring and control, can be determined by two reagent compositions delivered by two pumps: Free chlorine, total chlorine, and HPSI; Free chlorine, total chlorine, and pH; Free chlorine, pH, and phosphate (high range, 0 to 40 ppm); Free chlorine, anionic polymer, and phosphate (high range, 0 to 40 ppm); anionic polymer, phosphate (low range, 0 to 4 ppm), and phosphate (high range 0 to 40 ppm). When two reagent compositions are used in an online system, the first reagent composition that is designed for the first analyte can be used as an ancillary reagent of the second reagent composition for the determination of the second analyte. The functions of the ancillary solution include cleaning, providing buffer for the main reagent, and acting as a standard solution. For example, phosphate can be added into a reagent composition containing pH indicator for pH determination. Thus, the pH reagent composition is for pH analysis when it is used alone. It can be used as a phosphate standard to calibration a phosphate method.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the scope of the disclosure as defined by the following claims.

What is claimed is:

1. A method of determining at least two properties of a water sample using a multi-purpose reagent composition, the method comprising:

adding a multi-purpose reagent composition to an aqueous sample, said multi-purpose reagent composition comprising at least two reagents, wherein said reagents comprise a free chlorine sensitive dye, and a cationic dye;

measuring an absorbance of at least two different wavelengths of said aqueous sample after adding said multi-purpose reagent composition; and using said at least two absorbance measurements to determine said at least two properties of said aqueous sample, wherein said at least two properties comprise free chlorine concentration, and anionic polymer concentration.

2. The method of claim 1 wherein said free chlorine sensitive dye is a tetraalkyl benzidine compound.

3. The method of claim 2 wherein said free chlorine sensitive dye is N-(3-sulfopropyl)-3,3',5,5'-tetramethylbenzidine (TMB-PS).

4. The method of claim 1 wherein said cationic dye is selected from the group consisting of Dimethyl Methylene Blue (DMMB), Basic Blue 17, and New Methylene Blue (NMB).

5. The method of claim 1, wherein said multi-purpose reagent composition further comprises a co-solvent that is a water-soluble ketone.

6. The method of claim 1, wherein said multi-purpose reagent further comprises a phosphate reagent and said at least two properties further comprise phosphate concentration.

7. The method of claim 6 wherein said phosphate reagent comprises vanadomolybdate.

8. The method of claim 7 wherein said phosphate concentration is orthophosphate concentration.

9. A method of determining at least two properties of a water sample using a multi-purpose reagent composition, the method comprising:

adding a multi-purpose reagent composition to an aqueous sample, said multi-purpose reagent composition comprising at least two reagents, wherein said reagents comprise a free chlorine sensitive dye and a pH indicator;

measuring an absorbance of at least two different wavelengths of said aqueous sample after adding said multi-purpose reagent composition; and using said at least two absorbance measurements to determine said at least two properties of said aqueous sample, wherein said at least two properties comprise free chlorine concentration and pH.

10. The method of claim 9, wherein said free chlorine sensitive dye is an infrared dye.

11. The method of claim 10 wherein said infrared dye is selected from the group consisting of 2-[2-[2-chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide (IR-783), 1,1',3,3,3',3'-4,4',5,5'-di-benzo-2,2'-indotricarbocyanine perchlorate (IR-780), 2-[2-[2-chloro-3-[2-(1,3-dihydro-1,3,3-trimethyl-2H-indol-2-ylidene)-ethylidene]-1-cyclohexen-1-yl]-ethnyl]-1,3,3-trimethyl-3H-indolium chloride (IR-775), and 2-[7-[1,3-dihydro-3,3-dimethyl-1-(4-sulfobutyl)-2H-indol-2-ylidene]-hepta-1,3,5-trienyl]-3,3-dimethyl-1-(4-sulfobutyl)-3H-indolium hydroxide (IR-746).

12. The method of claim 9, wherein said pH indicator is selected from the group consisting of cresol red, phenol red, phenolphthalein, thymol blue, and O-cresolphthalein.

13. The method of claim 1, wherein said multi-purpose reagent composition further comprises a co-solvent that is a solvent mixture of ethylene glycol and methanol.

14. The method of claim 9 wherein said multi-purpose reagent further comprises a phosphate reagent and said at least two properties further comprise phosphate concentration.

15. The method of claim 14 wherein said phosphate reagent comprises vanadomolybdate.

16. The method of claim 15 wherein said phosphate concentration is orthophosphate concentration.

* * * * *

UNITED STATES PATENT AND TRADEMARK OFFICE
CERTIFICATE OF CORRECTION

| | | |
|---|---|---|
| PATENT NO. | : 9,228,986 B2 | |
| APPLICATION NO. | : 13/059139 | |
| DATED | : January 5, 2016 | |
| INVENTOR(S) | : Xiao et al. | |

It is certified that error appears in the above-identified patent and that said Letters Patent is hereby corrected as shown below:

Specification

In Column 3, Lines 8-9, delete "phosphates, in" and insert -- phosphates. In --, therefor.

In Column 5, Line 24, delete "N,N-bis(2" and insert -- N,N'-bis(2 --, therefor.

In Column 5, Lines 24-25, delete "N,N-bis(3" and insert -- N,N'-bis(3 --, therefor.

In Column 5, Line 48, delete "HPS-1." and insert -- HPS-1, --, therefor.

In Column 5, Line 60, delete "assay, in" and insert -- assay. In --, therefor.

In Column 6, Line 44, delete "0.2 ml" and insert -- 0.2 μm --, therefor.

In Column 7, Line 41, delete "monochlorame." and insert -- monochloramine. --, therefor.

In Column 7, Line 43, delete "monochlorame" and insert -- monochloramine. --, therefor.

In Column 7, Line 54, delete "five" and insert -- free --, therefor.

In Column 8, Line 11, delete "DUMB-HPSI" and insert -- DMMB-HPSI --, therefor.

In Column 8, Line 15, delete "predicted" and insert -- predicted HPSI --, therefor.

In Column 8, Line 26, delete "Table 1," and insert -- Table 1. --, therefor.

In Column 9, Line 4, delete "the indicator" and insert -- the pH indicator --, therefor.

In Column 9, Line 21, delete "during and" and insert -- during pH and --, therefor.

Signed and Sealed this
Twenty-sixth Day of July, 2016

Michelle K. Lee
*Director of the United States Patent and Trademark Office*

Specification

In Column 9, Line 55, delete "Table 2," and insert -- Table 2. --, therefor.

In Column 10, Line 18, delete "(Eq. 3)" and insert -- (Eq. 4) --, therefor.

In Column 10, Line 38, delete "IN light" and insert -- UV light --, therefor.

In Column 10, Line 45, delete "vanadomolybdate" and insert -- the vanadomolybdate --, therefor.

In Column 10, Line 64, delete "phosphate and one" and insert -- phosphate and HPS-I, one --, therefor.

In Column 11, Line 9, delete "mixing," and insert -- mixing --, therefor.

In Column 11, Line 11, delete "pH" and insert -- pH Reagent --, therefor.

Claims

In Column 13, Line 18, in Claim 3, delete "2" and insert -- 1 --, therefor.

In Column 14, Line 28, in Claim 13, delete "1," and insert -- 9, --, therefor.